United States Patent [19]

Faltynek

[11] Patent Number: 4,529,553
[45] Date of Patent: Jul. 16, 1985

[54] NICKEL COMPLEX CATALYST FOR HYDROSILATION REACTION

[75] Inventor: Robert A. Faltynek, Schenectady, N.Y.

[73] Assignee: General Electric Company, Waterford, N.Y.

[21] Appl. No.: 546,640

[22] Filed: Oct. 28, 1983

Related U.S. Application Data

[63] Continuation-in-part of Ser. No. 330,172, Dec. 14, 1981, abandoned.

[51] Int. Cl.³ .............................................. C07F 15/04
[52] U.S. Cl. ...................................... 556/12; 528/15; 528/30; 528/31; 528/32; 556/13; 556/18; 556/19; 556/20; 556/22; 502/158
[58] Field of Search .................... 260/439 R, 439 CY

[56] References Cited

U.S. PATENT DOCUMENTS

| | | | |
|---|---|---|---|
| 2,938,009 | 5/1960 | Lucas | 260/37 |
| 3,024,126 | 3/1962 | Brown | 106/308 |
| 3,159,601 | 12/1964 | Ashby | 260/46.5 |
| 3,159,662 | 12/1964 | Ashby | 260/46.5 |
| 3,220,972 | 11/1965 | Lamoreaux | 260/46.5 |
| 3,436,366 | 4/1969 | Modic | 260/37 |
| 3,635,743 | 1/1972 | Smith | 106/288 Q |
| 3,715,334 | 2/1973 | Karstedt | 260/46.5 UA |
| 4,012,399 | 3/1977 | Hechenbleikner et al. | 260/439 CY |
| 4,017,526 | 4/1977 | Wilke et al. | 260/439 CY |
| 4,029,629 | 6/1977 | Jeram | 260/37 SB |
| 4,041,010 | 8/1977 | Jeram | 260/42.26 |

FOREIGN PATENT DOCUMENTS 174585 10/1978 Czechoslovakia.

OTHER PUBLICATIONS

The Organic Chemistry of Nickel, vol. II, Academic Press, N.Y., 1975, pp. 69-72, Chapter VIII, The Hydrosilation and Hydrocyanation of Olefins, P. W. Jolly and G. Wills.
Chemistry Letters, 1973, pp. 781-782, Nickel(0)-Catalyzed Valence Isomerization of the 1,1'-Bishomocubane System, by Takaya, Yamakawa & Noyori.
Chem. Prum. 1976, 26(10), 522-4, Catalysis with Metal Complexes. XXXVIII. Selective Hydrosilylation of an Industrial $C_4$ Fraction from Pyrolysis, M. Capka, J. Hetflejs, & M. Vendelin.
Hydrosilylation of 1,3-Butadiene with Alkyl— and Alkoxysilanes Catalysed with Ni(II) and Ni(0) Compounds, M. Capka and J. Hetflejs, Col. Czech. Chem. Commun., vol. 40, 1975, p. 3020.
Novel Hydrosilylation of Butadiene Catalyzed by Palladium and Nickel Complexes, S. Takahashi, T. Shibano, H. Kojima and H. Hagihara, Organometal. Chem. Syn., 1, (1970/1971), pp. 193-202.

Primary Examiner—Helen M. S. Sneed

[57] ABSTRACT

Novel zero valent nickel complex catalysts have been developed for hydrosilation reactions including the use of such zero valent nickel complexes as catalysts in place of platinum complexes for SiH Olefin compositions to produce silicone elastomers. These zero valent nickel complex catalysts appear to be most effective under anaerobic conditions.

25 Claims, No Drawings

NICKEL COMPLEX CATALYST FOR HYDROSILATION REACTION

This application is a continuation-in-part of application Ser. No. 330,172, filed 12/14/81.

BACKGROUND OF THE INVENTION

The present invention relates to hydrosilation reactions and more particularly the present invention relates to the production of zero valent nickel complexes as catalysts for hydrosilation reactions.

Hydrosilation reactions have been known for a long time in silicone chemistry. Basically, such reactions comprise reacting a hydrogen-containing silane with an olefinic compound so as to add the hydrogen and silicon onto the olefinic group and form the desired compound. A more important role for such reactions has been to produce silicone elastomers. Such compositions comprise the utilization of a vinyl-terminated polysiloxane polymer in combination with a hydride-containing siloxane in the presence of a platinum catalyst to produce either at room temperature or at elevated temperatures a silicone elastomer. In such compositions, it was generally the practice to package the platinum catalyst with the vinyl siloxane but separate from the hydride siloxane. When it was desired to cure the composition, the two packages were mixed without an inhibitor and cured at room temperature to a silicone elastomer. Sometimes an inhibitor such as an alkenyl maleate, a hydroperoxide-containing compound or other well known inhibitor was utilized to extend the work life of the composition or to make it a one-package composition. By utilizing an inhibitor the composition could stay in the mixed state without curing at room temperature. However, upon being heated at an elevated temperature, that is a temperature above 100° C., the composition would cure to a silicone elastomer.

There was also the practice to incorporate various other ingredients such as, for instance, vinyl-containing resins composed of monofunctional siloxy units, tetrafunctional siloxy units and difunctional siloxy units. It was the purpose to utilize such vinyl-containing resins in such compositions as disclosed above to add to the strength of the cured composition without unduly increasing the uncured viscosity of the composition. It should be noted that such compositions are referred to in simple terms as SiH Olefin platinum catalyzed compositions. An example of such a composition is, for instance, to be found in Modic U.S. Pat. No. 3,436,366 which is hereby incorporated by reference. Note that in addition to the vinyl containing resins there may be utilized fillers. Reinforcing fillers such as fumed or precipitated silica or various types of extending fillers may be utilized whether treated or untreated as disclosed in Jeram U.S. Pat. No. 4,041,010 which is hereby incorporated by reference. As noted in the foregoing Jeram patent, the composition may contain fluorine substituent groups in the basic vinyl-containing polymer as well as the hydride cross-linking agent. The fluorine substituent groups give the composition exceptional solvent resistance.

As disclosed in the foregoing Jeram patent a hydrosiloxane cross-linking agent may be composed of various types of hydrides. Accordingly, there may be utilized as a cross-linking agent a hydride-containing resin composed of hydride-containing monofunctional siloxy units, and tetrafunctional siloxy units or a hydride-containing resin composed of hydride-containing monofunctional siloxy units, tetrafunctional siloxy units, and difunctional siloxy units. As noted in the foregoing Jeram patent, it was common to utilize many types of platinum catalysts in such reactions such as, for instance, from 1 to 100 ppm of the total composition could be a platinum catalyst wherein the platinum catalyst could be utilized as platinum deposited on solid carriers such as platinum on charcoal, or platinum on gamma-alumina or perhaps a solubilized platinum complex. A solubilized platinum complex was preferred in that the composition was more reactive. Accordingly, as disclosed in the foregoing Jeram patent, preferred platinum catalysts are those platinum compound catalysts which are soluble in the reaction mixture. The preferred platinum compounds can be selected from those having the formula

(PtCl$_2$.Olefin)$_2$ and

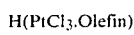

H(PtCl$_3$.Olefin)

as described in U.S. Pat. No. 3,159,601, Ashby. The olefin shown in the previous two formulas can also be any type of olefin but preferably an alkenylene having 2 to 8 carbon atoms, a cycloalkylene having 5 to 7 carbon atoms or styrene. Specific olefins that may be utilized in the above formulas are ethylene, propylene, the various isomers of butylene, octylene, cyclopentene, cyclohexene, cycloheptane, and so forth. A further platinum material usable in the composition of the present invention is the chloride cyclopropane complex (PtCl$_2$.C$_3$H$_6$)$_2$ described in U.S. Pat. No. 3,159,662, Ashby.

Still, further, the platinum containing material can be a complex formed from chloroplatinic acid with up to 2 moles of acid per gram atom of platinum of a member selected from the class consisting of alcohols, ethers, aldehydes and mixtures of the above as described in U.S. Pat. No. 3,220,972, Lamoreaux.

Another preferred platinum catalyst that may be utilized because of its higher reactivity is that disclosed in Karstedt U.S. Pat. No. 3,715,334. Generally speaking, this type of platinum complex is formed by reacting chloroplatinic acid containing 4 moles of water of hydration with tetravinylcyclotetrasiloxane in the presence of sodium bicarbonate in an ethanol solution.

Any type of platinum catalyst may be utilized in these reactions. However, the solubilized platinum complex catalyst as disclosed above such as the Karstedt and Lamoreaux catalyst are the preferred ones because of the high reactivity in promoting the addition reaction of the hydride to the vinylsiloxane.

The difference between two types of reactions in the instant case must be noted, that is, one wherein the hydride silane or siloxane adds on to an olefinic-containing compound which may be an organic compound to produce an intermediate compound which may be utilized in various types of processes or reactions. However, the other important type of reaction is the reaction of a hydrosiloxane resin or hydride-containing polysiloxane as disclosed in the foregoing Jeram patent in combination with a vinyl-containing polysiloxane to produce a silicone elastomer either at room temperature or elevated temperature. Such compositions can be utilized to produce molds, gasketing material, various types of fabricated products, etc.

By far the main catalyst that has been utilized in such reactions is a platinum catalyst. It should be noted that palladium and rhodium can also be utilized as a catalyst in such reactions but their costs are at least as high as the platinum. Accordingly, it is highly desirable to find a low cost catalyst for such reactions.

The complex bis(1,5 cyclo-octadienyl)nickel hereinafter called Ni(COD)$_2$ has been used as a soluble catalyst precursor for a variety of alkene transformations including polymerization as disclosed in P. W. Jolly and G. Wilkey, *The Organic Chemistry of Nickel*, Vol. II, Academic Press, New York, 1975, p 6; H. Takaya, M. Yamakawa, and R. Noyori, Chem. Lett. (1973) 781; M. Capka, Chem. Prum., 26 (1976) 522; and M. Capka and V. Macho, Czech. Patent 174,585. Such a catalyst has also been known for hydrosilation reactions, that is, adding a hydrogen-containing siloxanes onto an olefinic group of organic compounds as disclosed in the above references. However, the catalyst Ni(COD)$_2$, as far as has been known, has never been disclosed to be effective as a catalyst in the addition of a hydrosiloxane to a vinyl-containing polysiloxane.

It has unexpectedly been found that such a material is effective in an anaerobic system for the production of silicone elastomers. It has also been unexpectedly found that various types of phosphine nickel complex catalysts are effective as anaerobic catalysts in the addition of hydride groups of to olefinic groups in organic compounds or olefinic containing polysiloxane compounds. In the case where the nickel phosphine complex compounds are utilized as catalysts to react hydride-containing siloxanes with olefinic containing polysiloxanes, there results a silicone elastomer.

It is one object of the present invention to provide nickel complex catalysts for anaerobic systems in which hydrogen-containing silanes and hydrogen-containing siloxanes are reacted with olefin containing compounds.

It is an additional object of the present invention to provide an anaerobic system in which hydride-containing siloxanes are reacted with olefinic-containing polysiloxanes to produce silicone elastomers.

It is still an additional object of the present invention to provide for novel nickel complex catalysts.

It is yet an additional object of the present invention to provide a process for producing novel nickel complex catalysts.

It is still an additional object of the present invention to provide a process for forming silicone elastomers in anaerobic systems in which nickel complex catalysts are utilized to react hydrogen-containing siloxanes wih olefinic-containing polysiloxanes.

These and other objects of the present invention are accomplished by means of the disclosure set forth herein below.

SUMMARY OF THE INVENTION

In accordance with the above object, there is provided by the present invention a process using a zero valent nickel complex catalyst for hydrosilation reactions comprising a compound of the formula $$MNi^{(o)}G \qquad (1)$$

where M is a bidentate alkene cyclic hydrocarbon ring of $C_{8-12}$ and G is selected from monodentate and bidentate phosphorous groups having hydrogen atoms, substituted or unsubstituted hydrocarbon radicals or mixtures thereof bonded to the phosphorous atoms of said phosphorous groups.

A novel zero valent complex catalyst is provided by the present invention which has the formula

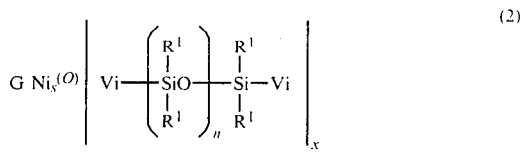

where G is selected from monodentate and bidentate phosphorous groups having hydrogen atoms, substituted or unsubstituted hydrocarbon radicals or mixtures thereof bonded to the phosphorous atoms of said phosphorous groups, s is a whole number that varies from 1 to 3, Vi is vinyl, $R^1$ is a $C_{1-8}$ monovalent hydrocarbon radical, n is a positive integer, preferably from 1 to 10 and x is a whole number that varies from 1 to 3. If x varies beyond 1 then s can also vary beyond 1. Such zero valent nickel complex catalysts are novel compounds which are effective in an anaerobic system for reacting hydrogen-containing siloxanes and hydrosilanes with olefinic compounds whether organic olefinic-containing compounds or olefinic polysiloxanes. In the case where the compound is an olefinic polysiloxane, then the reaction product is a silicone elastomer.

The present invention also encompasses the use of the known complex, Ni(COD)$_2$ as a complex catalyst for the anaerobic reaction of a hydride-containing siloxane with an olefinic-containing polysiloxane to produce a silicone elastomer. There is also encompassed by the present invention a process for producing the novel nickel complex catalyst discussed above.

DESCRIPTION OF THE PREFERRED EMBODIMENT

The nickel catalysts disclosed in the instant case are suitable as catalysts for anaerobic reactions and systems, that is, it has been found that the instant catalysts will decompose in the presence of oxygen and not function very effectively as hydrosilation catalysts. Accordingly, it should be understood that the present invention relates to the use of certain nickel catalysts as catalysts in hydrosilation reactions where the system is anaerobic, that is the system cures in the absence of oxygen. It should be noted that the present nickel catalyst can be utilized in the presence of oxygen; however, they are not nearly as effective in the presence of oxygen as they are under anaerobic conditions. Further, they tend to decompose in the presence of oxygen as will be set forth in the experiments at the end of this description.

It must also be appreciated that certain of the catalysts disclosed in the instant case have not been compounded before or invented prior to the instant case as far as is known and as such, they have not been used as catalysts for any type of hydrosilation reaction. Other catalysts within the scope of the instant invention have been disclosed previously as hydrosilation catalysts for simple hydrosilation reactions involving hydrogen containing silanes and an olefinic organic compound. However, they have not been disclosed as hydrosilation catalysts for systems comprising a vinyl-containing polysiloxane and a hydrogen containing siloxane so as to result in a silicone elastomer under anaerobic conditions.

The first catalyst that will be discussed in this section is the latter type of catalyst; that is, a catalyst which is known.

Such a catalyst has the formula $$M_2Ni^{(o)} \tag{3}$$

where M is a bidentate alkene cyclic hydrocarbon ring of $C_{8-12}$ atoms. Please note that in all the embodiments of the instant case the nickel catalyst is a zero valent nickel catalyst. The most preferred zero valent nickel catalyst is bis(1,5-cyclo-octadienyl)nickel. For reference purposes this shall hereinafter be referred to as $Ni(COD)_2$. Such a nickel catalyst is a known material which can be purchased from companies such as Strem Chemical Company, Newburyport, Mass. Such Ni(COD)$_2$ is obtained by reacting nickel acetylacetonate with 1,5-cyclo-octadiene and reducing agents in the presence of an ether solvent at a temperature of $-75°$ to $25°$ C. so as to yield $Ni(COD)_2$. However, if desired, it can be purchased from the foregoing chemical company as listed above. Further, the intermediates for producing this compound can also be purchased from the above company.

The reduction of nickel takes place in the presence of a reducing catalyst or agent which is preferably lithium triethylborohydride. The purpose of such a reducing agent will more fully be explained in the production of the other nickel compounds of the instant case. As stated previously, $Ni(COD)_2$ is a known material and it was known to use this catalyst in reactions in the addition of hydrogen-containing silanes onto an olefinic-organic compound. However, it was not known until the instant invention that this same catalyst can be utilized to add hydrogen-containing polysiloxane compounds to vinyl-containing polysiloxane compounds to produce silicone elastomers under anaerobic conditions. Accordingly, there is envisioned by the present invention a silicone composition that cures in an anaerobic state to a silicone elastomer comprising (A) 100 parts by weight of vinyl-terminated linear diorganopolysiloxane polymer having viscosity varying from 100 to 2,000,000 centipoise at 25° C. where the organic groups are a monovalent hydrocarbon radicals; from 1 to 50 parts by weight of a hydrogen-containing siloxane having a hydrogen content varying from 0.01 to 1% by weight and from 10 to 500 ppm of a zero valent nickel complex of the formula $M_2Ni^{(o)}$ where M is a bidentate alkene cyclic hydrocarbon ring of $C_{8-12}$. It should be noted in the foregoing formula given above and as previously defined, the preferred cyclic ring is 1,5-cyclooctadiene, that is a $C_8$ ring having two unsaturated bonds in it. Accordingly, the ring folds over and appends itself to the zero valent nickel by the two unsaturated bond areas through a chelate type of bonding system. The ring can also be $C_{10}$ and $C_{12}$. The ring can also be odd numbered within the scope of the invention. The $C_{9-12}$ zero valent nickel compounds are not known to have been produced; however, it is envisioned that they should be able to be produced in much the same way that the $C_8$ zero valent nickel compound was produced and would function the same way as a catalyst for the addition of a hydrogen-containing siloxane to a vinyl polysiloxane to form a silicone elastomer. It should also be noted that by the term "bidentate" is meant that the selected ring has two areas of bonding in a chelate type of bonding system. Accordingly, preferably as stated previously, the zero valent nickel complex has the formula $$(C_8H_{12})_2Ni^{(o)} \tag{4}$$

As a point of definition, there are two terms that are utilized in this description: monodentate and bidentate. Monodentate means the group which the term describes has a single bond, that is bonding with zero valent nickel through a single bond; bidentate means that the group which the term describes has two bonding areas with the zero valent nickel through a chelate type of bonding system. Proceeding now with a fuller description of the invention, preferably the vinyl-terminated polysiloxane has the formula $$\text{Vi}-\underset{R^3}{\overset{R^2}{\underset{|}{\text{SiO}}}}-\left[\underset{R^3}{\overset{R^2}{\underset{|}{\text{SiO}}}}\right]_x-\underset{R^3}{\overset{R^2}{\underset{|}{\text{Si}}}}-\text{Vi} \tag{5}$$

where Vi is vinyl, $R^2$ is a monovalent hydrocarbon radical, $R^3$ is a monovalent hydrocarbon radical that does not contain aliphatic unsaturation, and z varies such that the viscosity of the polymer varies from 100 to 2,000,000 and preferably from 100 to 500,000 centipoise at 25° C. Please note that $R^2$ can be any monovalent hydrocarbon radical including olefinic hydrocarbon radicals such as, for instance, alkyl radicals such as methyl, ethyl, propyl, etc.; cycloalkyl radicals such as cyclohexyl, cycloheptyl, etc.; mononuclear aryl radicals such as phenyl, methylphenyl, ethylphenyl, etc.; fluoroalkyl radicals such as 3,3,3-trifluoropropyl, and alkenyl radicals such as vinyl, allyl, etc. The $R^3$ radicals can be any of the above radicals except the alkenyl radicals. Preferably, the vinyl is only bonded to the terminal silicon atoms; however, as stated previously, the vinyl unsaturation can be on the polymer chain as well as on the terminal silicon atoms. Preferably, the vinyl-terminated polysiloxane polymer has a vinyl content that varies from 0.01 to 0.6 weight percent.

There may also be present in the composition from 10 to 200 parts by weight of filler. The filler may either be reinforcing filler selected from fumed silica and precipitated silica or may be an extending filler such as lithopone, zinc oxide, iron oxide, glass fibers, diatomaceous earth, silica aerogel, crushed quartz, and so forth. The silica fillers may be treated with cyclopolysiloxane as disclosed in Lucas U.S. Pat. No. 2,938,009 or as disclosed in Brown U.S. Pat. No. 3,024,125 or Smith U.S. Pat. No. 3,635,743. Other types of treatments are disclosed in various types of patents that are present in this area. Suffice it to state that any type of filler can be utilized in the instant composition, preferably treated so as to enhance the physical properties of the cured composition without unduly increasing the viscosity of the uncured composition. Preferably, the filler is treated both with cyclopolysiloxanes and silazanes. For more information on the treatment of fillers, one is referred to the disclosure of U.S. Pat. No. 4,041,010 and other patents in the area.

The other necessary ingredient in the composition of the instant case is the hydrogen-containing siloxane. The hydrogen-containing siloxane comprises a hydride-containing resin having

(6)

units and SiO₂ units where the ratio of H+R⁴ to Si varies from 1.0 to 1, to 2.7 to 1, and R⁴ is a monovalent hydrocarbon radical free of aliphatic unsaturation. The radical R⁴ can be any of the monovalent hydrocarbon radicals previously discussed for R² and R³ except it cannot be an alkenyl radical. Such hydrosiloxane resins are well known.

Another type of hydrogen-containing siloxane resin that can be utilized as a cross-linking agent in the compositions of the instant case, comprises a hydride resin having

(6)

units and R₂⁴ SiO units and SiO₂ units where the H+R⁴ to Si ratio varies from 1.2 to 1 to 2.7 to 1 and R⁴ is a monovalent hydrocarbon radical free of aliphatic unsaturation. The radical R⁴ can be any of the monovalent hydrocarbon radicals given previously for the R² and R³ radicals except an olefinic radical.

Finally, the cross-linking agent may be a hydride-containing linear polysiloxane having the formula

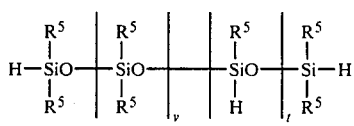
(7)

where R⁵ is a monovalent hydrocarbon radical free of aliphatic unsaturation, v and t vary such that the viscosity of the polymer varies from 10 to 1,000 centipoise at 25° C. and more preferably varies from 10 to 100 centipoise at 25° C. Preferably, this polymer is such that it has hydrogen groups bonded to the terminal silicon atoms, and also hydrogen groups on the siloxane polymer chain. The radical R⁵ can be any of the monovalent hydrocarbon radicals previously given for R² and R³ except desirably it is a radical free of olefinic unsaturation. It should be noted that there can be olefinic unsaturation in the hydride resins and the hydrogen-polysiloxane if the nickel catalyst is not packaged with the hydride resin. Generally, the hydrogen content of the hydride cross-linking agent may vary from 0.01 to 1.0% by weight. If the hydride resin or hydride linear polysiloxane has olefinic unsaturation and the nickel catalyst is packaged with it, the composition will cross-link with itself to form a silicone elastomer. However, the more common system is that the hydrides do not contain olefinic unsaturation and normally the nickel catalyst may be packaged as a two-package system with the hydride-containing compound in one package and the vinyl polymer with the nickel catalyst in a second package, and when it is desired to cure the composition, the two packages are mixed and the composition cures in an anaerobic system to a silicone elastomer with good physical properties. For more information as to the vinyl-siloxane and the hydride cross-linking agents, one is referred to the disclosure of Jeram U.S. Pat. No. 4,041,010 and U.S. Pat. No. 4,029,629 which is hereby incorporated by reference. Suffice it to state that workers skilled in the art can refer to these patents as well as any other patents in the area of preparation of silicone elastomers by reacting hydride resins and hydride-containing linear polysiloxanes with vinyl polysiloxanes to produce silicone elastomers. The details for producing the vinyl-siloxane as well as the hydride-containing siloxane resins and the linear hydride-containing polysiloxane is to be found in the foregoing Jeram patents and elsewhere as is well known to a worker skilled in the art.

There may also be in the composition per 100 parts of the vinyl siloxane from 20 to 50 parts by weight of an organopolysiloxane copolymer of $R_3''SiO_{0.5}$ units and SiO₂ where R'' is a member selected from a class consisting of vinyl radicals and monovalent hydrocarbon radicals free of aliphatic unsaturation where the ratio of $R_3''SiO_{0.5}$ units to SiO₂ is from 0.5 to 1 to 1 to 1 and from about 2.5 to 10 mole percent of the silicon atoms contain silicon bonded vinyl groups.

In addition to this resin, there may be utilized a vinyl-containing resin in which there are also $R_2''SiO$ units where the ratio of $R_3''SiO_{0.5}$ units to the SiO₂ units is between 0.5 to 1 and 1 to 1 and the $R_2''SiO$ units are preferably present in an amount equal to from about 1 to 10 mole percent based on the total number of moles of the siloxane units in the copolymer, wherein the silicon bonded vinyl groups are present in an amount equal to from about 2.5 to 10 mole percent of the copolymer resin compound. For more information as to the production and use of such vinyl-containing resins, one is referred to the disclosure of Modic U.S. Pat. No. 3,436,366 which is hereby incorporated by reference as well as the foregoing Jeram patents. It should be noted that the foregoing vinyl-containing resins and hydride-containing resins and hydride linear containing polysiloxane are generally produced by hydrolyzing the appropriate chlorosilanes in water and then purifying the hydrolyzates that are produced.

It now becomes important to note two special types of catalysts that have been developed and produced in the instant invention which as far as is known, have not been disclosed previously in the art.

First there comprises a compound of the formula $$MNi^{(n)}G \qquad (8)$$

where M is a bidentate alkene or alkyne cyclic hydrocarbon ring of C₈ to C₁₂ and G is selected from monodentate and bidentate phosphorous groups having hydrogen atoms, substituted or unsubstituted hydrocarbon radicals or mixtures thereof bonded to the phosphorous atoms of said phosphorous groups. Again, M can be any of the bidentate, alkene and alkyne radicals previously disclosed for the previous catalyst. However, it is preferably 1,5-cyclooctodienyl. It should be noted that in this case it is stated that M can be anywhere from C₈₋₁₂ and is most preferably C₈. However, C₉–C₁₂ alkene and alkyne cyclic hydrocarbon rings will also operate in the present invention with respect to this nickel catalyst. The nickel catalyst is a zero valent nickel and the cyclic bidentate alkene or alkyne ring appends itself to the zero valent nickel through two chelate type bonding systems, that is the portions of the cyclic hydrocarbon ring which have the unsaturation. The cyclic ring should have two unsaturated areas whether it contains 9,10, 11, or 12 carbon atoms. It is envisioned that C$_9$–C$_{12}$ rings should also work to produce the appropriate cyclic appendage in a zero valent nickel in accordance with the instant invention. G in the above formula is selected from monodentate and bidentate phosphorous groups having hydrogen atoms, substituted or unsubstituted hydrocarbon radicals, or mixtures thereof bonded to the phosphorous atoms of said phosphorous groups. Preferably the phosphorous-bonded substituents are alkyl radicals or aryl radicals and most preferably are mononuclear aryl radicals. One of the monodentate phosphorous groups can be R$_3$P such that G is equal to (R$_3$P)$_2$. In this case there are needed two phosphorous groups to append themselves to the zero valent nickel in order to satisfy the coordination number of the zero valent configuration. In the foregoing formula for the R$_3$P group R is selected from the class consisting of hydrogen, and substituted or unsubstituted hydrocarbon radicals, preferably alkyl radicals and aryl radicals having 1 to 8 carbon atoms, and mixtures thereof.

Specific examples of monodentate radicals which G can be are radicals of the formula, $$[(C_6H_5)_3P]_2 \qquad (9)$$

$$(PH_3)_2, ((C_2H_5)_3P)_2,$$

$$((CF_3CH_2CH_2)_3P)_2, ((C_3H_7)_2PH)_2,$$

$$((C_6H_5)(CH_3)PH)_2$$

and the like.

The foregoing formulas given above for G are well within the scope of the first formula for the group, R$_3$P.

However, a more complex type of phosphorous bidentate compound having the general formula $$R_2^6P\text{-}(R^7)_n\text{-}PR_2^6$$

where R$^6$ is the same as R and R$^7$ is a divalent substituted or unsubstituted hydrocarbon radical and n is equal to 1 to 20, preferably 1 to 6 and most preferably 2 or 3, can be appended to the zero valent nickel. For instance, G can be the bidentate radical such as, $$(C_6H_5)_2P(CH_2)_2P(C_6H_5)_2$$

$$H_2P(CH_2)_2PH_2,$$

$$(CH_3)_2P(CH_2)_3P(CH_3)_2,$$

$$(CF_3CH_2CH_2)_2P(CH_2)_2P(CH_2CH_2CF_3)_2$$

$$(C_2H_5)(H)P(CH_2)_4P(H)(C_2H_5),$$

$$(C_6H_5)_2P(CH_2)_2PH_2,$$

$$(C_2H_5)(CH_2CH_2CF_3)P(CH_2)_5P(H)(C_6H_5) \qquad (10)$$

and the like.

As noted, the formula of the above compound which for reference purposes can be referred to as a diphosphorous compound, is a bidentate compound which forms a ring structure in which the two phosphorous atoms are appended to the zero valent nickel through chelate type of bond systems. Bidentate complexes within the scope of the present invention are more preferred than monodentate complexes within the scope of the present invention because the resulting nickel complex will be more stable.

The foregoing compounds are novel for utilization in hydrosilation reactions in an anaerobic system involving the reaction of a hydrogen-containing silane or vinyl-containing siloxanes. Accordingly, in the broadest generic coverage of the instant invention, the above zero valent nickel catalysts can be utilized as catalysts in anaerobic systems where the hydrogen group of a hydrogen-containing silane or siloxane is added on to an olefinic diorganopolysiloxane. It should be noted that these novel catalysts should be utilized under anaerobic conditions since they will decompose when exposed to oxygen and thus are not very effective in yielding silicone elastomers in the presence of oxygen. However, the use of such catalysts in an oxygen containing system is not precluded and is within the intended scope of the present invention. Such compounds are made by reacting a compound of the formula, $$Q_2NiG \qquad (11)$$

where Q is a halogen radical and is most preferably chlorine and G is as previously defined. This reaction takes place by first taking the foregoing reactant and treating it with a reducing agent. One example of a reducing agent is, for instance, lithium triethylborohydride. Other reducing agents that can be utilized are for instance sodium borohydride, lithium aluminum hydride or potassium hydride. After the above halogen compound is reduced to a zero valent nickel, there is added to the reaction mixture a bidentate unsaturated cyclic hydrocarbon ring of C$_{8-12}$ atoms. The reaction in the instant case is carried out in the absence of oxygen and preferably under a nitrogen atmosphere by first reducing the halogenated nickel compound to the a zero valent state and then adding to the reaction mixture a bidentate alkene or alkyne cyclic hydrocarbon ring of C$_{8-12}$. Preferably, the reactions are carried out at a temperature range of −75° to 25° C. under atmospheric pressure. More preferably the reactions are carried out at a temperature of 0° to 25° C. at atmospheric pressure.

At least two moles of the reducing agent is needed per mole of the nickel reactants since this is necessary to reduce the dichloro nickel compound to a zero valent nickel compound. It is also preferable to utilize a solvent in the reaction mixture. Examples of solvents are, for instance, diethyl ether, dibutyl ether and tetrahydrofuran. Generally the solvent may be selected from dialkyl ethers, diarylethers, or cyclic ethers. It should be noted that almost any ether solvent can be utilized as a solvent in the reaction media. Preferably there is utilized a solvent so as to allow intimate mixing of the reactants and so as to carry out the proper reduction of the nickel compound. The reaction takes place in the period of time varying anywhere from 30 minutes to 4 hours—more preferably from 30 minutes to 2 hours.

In addition, any of the starting materials for the above reactions can be obtained from the Strem Chemical Company, Newburyport, Mass., and the Aldrich Chemical Company, Milwaukee, Wisc. After having those starting materials as noted above, the foregoing preferred nickel catalysts of the instant case can be obtained in accordance with the above reactions and processes.

A novel zero valent nickel catalyst provided by the instant invention is a compound of the formula

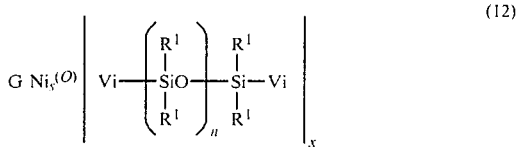

(12)

where G is as previously defined, s is a whole number that varies from 1 to 3, Vi is vinyl, $R^1$ is a $C_{1-8}$ monovalent substituted or unsubstituted hydrocarbon radical n is a positive integer, preferably from 1 to 10, and x is a whole number that varies from 1 to 3. The vinyl siloxane in the above formula preferably is a disiloxane and preferably is vinyl terminated. The radical $R^1$ can be any $C_{1-8}$ monovalent organic radical preferably free of aliphatic unsaturation and is most preferably an alkyl radical of 1–8 carbon atoms such as methyl. As noted in the above formula, s can vary from 1 to 3 and x can vary from 1 to 3. It is believed that more than one nickel is present in a single molecule and in some cases up to a total of 3 nickel atoms may be present When this happens, the vinyl siloxane is also present up to a total of 3 times in a single molecule.

In this zero valent nickel complex the vinyl groups in the siloxane form chelate type linkages with the zero valent nickel in a ring structure. Thus, accordingly, the vinyl siloxane folds over such that the vinyl groups form a chelate type of bidentate linkage with the zero valent nickel. Such vinyl siloxane, zero valent nickel complex catalyst can be formed with any of the monodentate and bidentate phosphorous groups given previously for G.

Such novel zero valent nickel complexes are formed by reducing a compound of the formula

$$GNiQ_2 \tag{13}$$

where Q is a halogen radical and G is selected from monodentate and bidentate phosphorous groups as previously defined with a reducing agent and then adding to the reaction a mixture of bidentate siloxane compound of the formula,

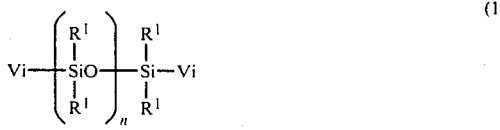

(14)

where Vi is vinyl, n is a positive integer, preferably 1 to 10 and $R^1$ is a $C_{1-8}$ substituted or unsubstituted hydrocarbon radical wherein the entire reaction takes place in the absence of oxygen. Preferably $R^1$ is not an olefinic radical.

Again, the reaction takes place in the absence of oxygen and preferably in a nitrogen atmosphere, the reaction time being anywhere from 30 minutes to 4 hours and more preferably being from 30 minutes to 2 hours. Any of the reducing agents utilized for the previous reaction can be utilized in this process, the preferred reducing agent being lithium triethylborohydride. There is utilized at least 2 moles of the reducing agent per mole of the halogenated nickel reactant since it will take two moles of the reducing agent to reduce one mole of the halogenated nickel reactant to the zero valent state. Again, preferably, the reaction takes place anywhere from $-75°$ to $25°$ C. and more preferably takes place at a temperature of $0°$ to $25°$ C. The solvent can be any type of ether as stated previously. The ether solvent can be selected from diethyl ether, di-n-butyl ether and tetrahydrofuran.

Once the novel zero valent nickel complex is obtained, it is kept stored in the absence of oxygen, since it will decompose upon being exposed to oxygen. It is then anaerobically incorporated into a vinyl siloxane and the package is stored in the absence of air. When the vinyl siloxane catalyst package is mixed with the hydrogen-containing siloxane in the absence of air, it cures to form a silicone elastomer.

It should be noted that there is broadly disclosed in the instant case that the novel zero valent nickel complexes may be utilized as catalysts in any hydrosilation reaction as distinguished from the $Ni(COD)_2$ catalyst. More preferably, the zero valent nickel complexes of the instant case are utilized as catalysts in silicone compositions that cure to silicone elastomers. Such a system comprises (A) 100 parts by weight of a vinyl terminated linear diorganopolysiloxane polymer with a viscosity varying from 100 to 2,000,000 centipoise at $25°$ C. with the organic groups being monovalent substituted or unsubstituted hydrocarbon radical; (B) from 1 to 50 parts by weight of a hydrogen-containing siloxane wherein the hydrogen content varies from 0.1 to 1.0 percent by weight; and (C) from 10 to 500 parts per million Ni as contained in the novel zero valent nickel complex of the instant case. In such compositions the reactants may all be the same and in the same quantitites as given before for the $Ni(COD)_2$ system except that the catalyst is the novel nickel complex of the instant case. Accordingly, the description given previously for the $Ni(COD)_2$ system applies to the zero valent nickel complexes disclosed above in terms of types of vinyl siloxane, hydrogen-containing siloxanes, vinyl resins, fillers, and other additives that may be present in the composition and also in the preparation of the composition in two packages as the case may be. Accordingly, the description of the individual ingredients will not be repeated here since it was given out previously with respect to the $Ni(COD)_2$ system. However, it must be emphasized again that the present novel nickel complexes unlike the $Ni(COD)_2$ are novel compounds and as such, they are disclosed for utilization generically as hydrosilation catalysts for any type of hydrosilation reaction with organic-containing olefinic compounds as well as olefinic containing polysiloxane compounds and with hydrogen containing silanes as well as with hydrogen containing polysiloxanes under anaerobic conditions.

The Examples below are given for the purpose of illustrating the present invention. They are not given for the purpose of setting or defining any limits or boundaries to the instant invention. All the parts in the Examples are by weight.

EXAMPLE

In the Examples below $Ni(COD)_2$ refers to bis(1,5-cyclo-octadienyl) zero-valent nickel and the reference to the complex DIPHOS refers to 1,2-bis(diphenylphosphino)ethane, while DVTMDS refers to divinyltetramethyldisiloxane.

The $Ni(COD)_2$ material was purchased from Strem Chemical Company, Newburyport, Mass., and it was of sufficient purity as received to be air stable for a few minutes. Small particles and metallic nickel catalyzed decomposition of the complex. There was reduction of Cl₂NiDIPHOS with two equivalents of LiBEt₃H (Et stands for ethyl) in tetrahydrofuran at −78° C. followed by addition of 1,5 cyclo-octadiene. This was followed by warming to room temperature and solvent removal gave a highly air sensitive tan solid with spectral characteristics of Ni(COD) (DIPHOS). Similar reduction of Cl₂Ni(PPh₃)₂ with subsequent addition of DVTMDS yielded yellow pyrophoric (Ph₃P)₂Ni(DVTMDS)$_x$. (Ph stands for phenyl.)

These three nickel complex catalysts which were either purchased or prepared as explained above were tested in a common SiH olefin system in which formerly a platinum catalyst was utilized. Such system comprised 75 parts by weight of vinyl-terminated dimethylpolysiloxane polymer having a viscosity of 3500 centipoise at 25° C. In this vinyl-terminated polymer, there was also present 25 parts by weight of a resin composed of methyl vinyl monofunctional siloxy units, SiO₂ units, and vinylmethylsiloxy difunctional siloxy units wherein the vinyl-containing resin had 2.5 mole percent of vinyl in it. One hundred parts of the foregoing vinyl polymer with the vinyl resin was mixed with 100 parts of a composition composed of 50 parts of the same vinyl-terminated polysiloxane that was present in the first package, and there was also in the second package 50 parts of a hydride-containing polysiloxane resin composed of H-dimethyl-siloxy monofunctional units and SiO₂ units where there were two of the monofunctional siloxy units to one of the tetrafunctional siloxy units, and wherein the resin had about 0.9 percent by weight of hydrogen. The two parts were mixed, that is 100 parts of the first mixture was mixed with 100 parts by weight of the second mixture and then into the resulting mixture there was added 0.001 parts of the nickel complex per two parts of the silicone composition. In terms of nickel concentration, this is in the range of 50 to 100 ppm nickel in a 2 gram test sample. All three complexes at this concentration range promoted RTV gelation in 24 hours in aluminum pans in an oxygen-free atmosphere within a Vacuum Atmospheres dry box. (A dry box is a closed chamber containing a nitrogen atmosphere that is continually circulated and scrubbed of traces of oxygen.)

There was less than 10 ppm of oxygen in the continuously circulating atmosphere of the drybox. Similar samples were mixed in two dram bottles with screw tops in a drybox and removed to ambient atmosphere. For all three catalysts, essentially the same behavior was observed. Some gelation occurred in the 24 hours following uncapping in the air, but the silicone composition never became tack-free. Dark coloration was noted in time strongly suggesting catalyst decomposition. A test run at 150° C. using Ni(COD)(DIPHOS) gave a tack-free gel in two hours in air (with some coloration/decomposition). But the same experiment using (PH₃P)₂Ni (DVTMDS)$_x$ failed to give any gel in four hours (coloration/decomposition evident).

The above experimental results indicate that the foregoing nickel complex will promote the formation of silicone compositions from SiH Olefin ingredients that were previously catalyzed with platinum catalysts to produce silicone elastomers. However, at the present time, these novel nickel complex catalysts as well as the Ni(COD)₂ were indicated to be effective catalysts only under anaerobic conditions to produce silicone elastomers from SiH Olefin compositions.

What is claimed is:

1. A composition of matter useful as a hydrosilation catalyst, comprising a compound of the formula

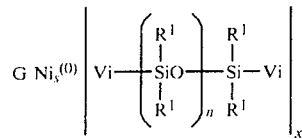

where G is selected from monodentate and bidentate phosphorous groups having hydrogen atoms, halogen substituted or unsubstituted hydrocarbon radicals or mixtures thereof bonded to the phosphorous atoms of said phosphorous groups, s is a whole number that varies from 1 to 3, x is a whole number that varies from 1 to 3, n is a positive integer, Vi is vinyl and R¹ is a C₁₋₈ monovalent hydrocarbon radical.

2. The composition of claim 1 wherein G has the formula (R₃P)₂ where R is selected from the group consisting of hydrogen, halogen substituted and unsubstituted monovalent hydrocarbon radicals and mixtures thereof.

3. The composition of claim 2 wherein R is selected from alkyl radicals and aryl radicals having from 1 to 8 carbon atoms.

4. The composition of claim 2 wherein R is a mononuclear aryl radical.

5. The composition of claim 2 wherein R is a phenyl radical.

6. The composition of claim 1 wherein G has the general formula (R⁶)₂P-(R⁷)$_n$-P(R⁶)₂ where R⁶ is selected from the group consisting of hydrogen, halogen substituted and unsubstituted monovalent hydrocarbon radicals and mixtures thereof, R⁷ is a divalent substituted or unsubstituted hydrocarbon radical and n is an integer of from 1 to about 20.

7. The composition of claim 6 wherein n is an integer of from 1 to about 6.

8. The composition of claim 6 wherein n is an integer equal to 2 or 3.

9. The composition of claim 6 wherein R⁶ is selected from alkyl radicals and aryl radicals having from 1 to 8 carbon atoms.

10. The composition of claim 6 wherein R⁶ is a mononuclear aryl radical.

11. The composition of claim 6 wherein R⁶ is a phenyl radical.

12. The composition of claim 8 wherein R⁷ is —CH₂—.

13. The composition of claim 12 wherein R⁶ is a phenyl radical.

14. The composition of claim 1 wherein n is an integer of from 1 to about 10.

15. The composition of claim 1 wherein n equals 1.

16. A process for forming a zero valent nickel complex comprising (A) reacting (1) a compound of the formula Q₂Ni$^{(O)}$G where Q is a halogen radical and G is selected from monodentate and bidentate phosphorous groups having hydrogen atoms, halogen substituted or unsubstituted hydrocarbon radicals or mixtures thereof bonded to the phosphorous atoms of said phosphorous groups, with (2) a reducing agent and then (B) adding to the reaction mixture a siloxane compound of the formula

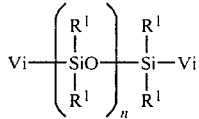

where Vi is vinyl, n is a positive integer and $R^1$ is a $C_{1-8}$ monovalent hydrocarbon radical and wherein the entire reaction takes place in the substantial absence of moisture.

17. The process of claim 15 wherein the reducing agent is lithiumtriethylborohydride.

18. The process of claim 15 wherein there is utilized at least two moles of reducing agent per mole of halogenated nickel reactant.

19. The process of claim 17 wherein the reaction is carried out at a temperature in the range of $-75°$ to $25°$ C. and at atmospheric pressure.

20. The process of claim 18 wherein the reaction takes place for a period of time ranging from 30 minutes to 4 hours under a nitrogen atmosphere.

21. The process of claim 15 wherein G has the general formula $$(R_3P)_2$$

where R is selected from the group consisting of hydrogen, halogen substituted or unsubstituted monovalent hydrocarbon radicals and mixtures thereof.

22. The process of claim 15 wherein G has the general formula $$(R^6)_2P\text{-}(R^7)_n\text{-}P(R^6)_2$$

where $R^6$ is selected from the group consisting of hydrogen, halogen substituted and unsubstituted monovalent hydrocarbon radicals and mixtures thereof, $R^7$ is a divalent substituted or unsubstituted hydrocarbon radical and n is an integer of from 1 to about 20.

23. The process of claim 15 wherein the reaction takes place in the presence of an ether solvent.

24. A composition of matter useful as a hydrosilation catalyst, comprising a compound of the formula

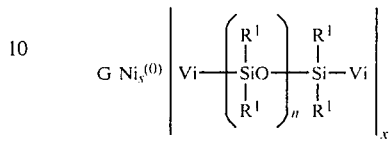

where G is selected from monodentate and bidentate phosphorous groups having hydrogen atoms, substituted or unsubstituted hydrocarbon radicals or mixtures thereof bonded to the phosphorous atoms of said phosphorous groups, s is a whole number that varies from 1 to 3, x is a whole number that varies from 1 to 3, n is a positive integer, Vi is vinyl and $R^1$ is a $C_{1-8}$ monovalent hydrocarbon radical.

25. A process for forming a zero valent nickel complex comprising (A) reacting (1) a compound of the formula $$Q_2Ni^{(O)}G$$

where Q is a halogen radical and G is selected from monodentate and bidentate phosphorous groups having hydrogen atoms, substituted or unsubstituted hydrocarbon radicals or mixtures thereof bonded to the phosophrous atoms of said phosphorous groups, with (2) a reducing agent and then (B) adding to the reaction mixture a siloxane compound of the formula

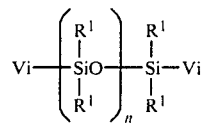

where Vi is vinyl, n is a positive integer and $R^1$ is a $C_{1-8}$ monovalent hydrocarbon radical and wherein the entire reaction takes place in the substantial absence of moisture.

* * * * *